United States Patent [19]

Baird et al.

[11] 4,108,867

[45] Aug. 22, 1978

[54] 2-AMINOTHIOPHENES

[75] Inventors: David Boyd Baird; Alan Thomas Costello; Brian Ribbons Fishwick; Robert David McClelland; Peter Smith, all of Manchester, England

[73] Assignee: Imperial Chemical Industries Limited, London, England

[21] Appl. No.: 466,059

[22] Filed: May 1, 1974

Related U.S. Application Data

[63] Continuation-in-part of Ser. No. 324,190, Jan. 16, 1973, abandoned.

[30] Foreign Application Priority Data

Jan. 28, 1972 [GB] United Kingdom ............... 4046/72
Jan. 8, 1973 [GB] United Kingdom ................ 965/73

[51] Int. Cl.² .................... C07D 333/24; A01N 9/00; C09B 27/00
[52] U.S. Cl. .................... 260/332.2 C; 260/329 S; 260/332.3 C; 424/275; 8/41 R
[58] Field of Search .................... 260/332.2 C, 329 S, 260/332.3 C

[56] References Cited

U.S. PATENT DOCUMENTS 3,636,062  1/1972  Singer .......................... 260/332.2 C

OTHER PUBLICATIONS

Gewald, "Chemical Abstracts", vol. 64 (1966) p. 3451 b.

Primary Examiner—A. Siegel
Attorney, Agent, or Firm—Cushman, Darby & Cushman

[57] ABSTRACT

The compounds of the formula

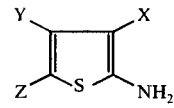

wherein
X is a lower alkylsulphonyl, phenylsulphonyl, cyano, carbonamido, carboxylic acid or carboxylic acid ester group;
Y is hydrogen, lower alkyl, phenyl or nitrophenyl; and
Z is nitro, cyano or carbonamido.

6 Claims, No Drawings

2-AMINOTHIOPHENES

This application is a continuation-in-part of our application Ser. No. 324,190 which was filed in the United States Patent Office on Jan. 16, 1973 now abandoned.

This invention relates to heterocyclic compounds of the thiophene series which are valuable as dyestuffs intermediates or as biocides.

According to the invention there are provided the compounds of the formula:

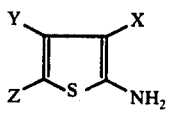

wherein
X is a lower alkylsulphonyl, phenylsulphonyl, cyano, carbonamido, carboxylic acid or carboxylic acid ester group;
Y is hydrogen, lower alkyl, phenyl or nitrophenyl; and
Z is nitro, cyano or carbonamido.

Throughout this Specification the terms "lower alkyl" and "lower alkoxy" are used to denote alkyl and alkoxy radicals respectively containing from 1 to 4 carbon atoms.

The carbonamido groups represented by X and Z are of the formula

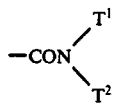

wherein $T^1$ is hydrogen, lower alkyl or phenyl, and $T^2$ is hydrogen or lower alkyl, such as carbonamido, N-methylcarbonamido, N:N-diethylcarbonamido and N-phenylcarbonamido groups.

As examples of the lower alkyl radicals represented by Y, $T^1$ and $T^2$ there may be mentioned methyl, ethyl, n-propyl and n-butyl.

As examples of the lower alkylsulphonyl groups represented by X there may be mentioned methylsulphonyl and ethylsulphonyl.

The carboxylic acid ester groups represented by X are preferably lower alkoxycarbonyl groups such as methoxycarbonyl, ethoxycarbonyl and n-butoxycarbonyl and lower alkoxy lower alkoxycarbonyl groups such as β-(methoxy- or ethoxy-) ethoxycarbonyl and γ-ethoxypropoxycarbonyl groups.

Preferably X is cyano, carbonamido, carboxylic acid, lower alkoxycarbonyl or lower alkoxy lower alkoxycarbonyl.

Preferably Z is the nitro group.

The compounds of the invention wherein Z is a nitro group can be obtained by nitration of the corresponding N-acylamino compounds of the above formula wherein Z is hydrogen, followed by hydrolysis of the N-acylamino compound. The nitration can be carried out in sulphuric acid medium preferably at temperatures in the range of −5° to 10° C, or in a mixture of acetic acid and acetic anhydride at 35° to 40° C. The subsequent hydrolysis is then effected by heating in a dilute aqueous solution of an acid such as sulphuric acid. When compounds are used in the nitration wherein Y is phenyl or substituted phenyl, then the nitration frequently results in the introduction of a second nitro group into this phenyl radical particularly when the nitration is effected in sulphuric acid.

However when X is a carboxylic acid group the nitration must be carried out under such conditions that only one nitro group is introduced into the thiophene ring as there is a tendency for the carboxylic acid group to be replaced by a second nitro group.

The compounds wherein X and/or Z represents a carbonamido group can be obtained by converting the corresponding N-acylamino compounds of the above formula wherein X and/or Z is a carboxylic acid group to the corresponding acid chloride by treatment with thionyl chloride in an inert solvent such as toluene, reacting the resulting acid chloride with the appropriate amine of the formula

followed by hydrolysis of the N-acylamino group.

When the carboxylic acid ester group represented by X is other than a lower alkoxycarbonyl group, then such compounds can be conveniently obtained by ester interchange which involves reacting one of the said compounds wherein X is a lower alkoxycarbonyl group, or the corresponding N-acyl derivative, with the appropriate alcohol, such as β-methoxyethanol, β-ethoxyethanol or γ-ethoxypropanol presence of a catalyst such as tetra-n-butyltitanate, and when starting from the N-acyl derivative subsequently removing the acyl group by hydrolysis.

The compounds wherein Z is a cyano group can be prepared from the corresponding N-acyl compounds wherein Z is a hydrogen atom by reaction with phosphoryl chloride and N-methylformanilide to give the corresponding N-acyl compound wherein Z is formyl which on conversion to the oxime followed by treatment with acetic anhydride gives the cyano compound which is then de-acylating in conventional manner.

The compounds wherein X is other than a carbonamido or carboxylic acid group, Y is lower alkyl and Z is a carbonamido group can be obtained by reacting a cyano compound of the formula $XOOC.CH_2CN$ wherein X is other than carbonamido or carboxylic acid with an amide of the formula

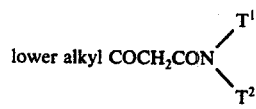

wherein $T^1$ and $T^2$ have the meanings stated, and with sulphur in ethanol medium containing a base such as diethylamine.

The compounds wherein X and/or Z is a $-CONH_2$ group can be obtained by mild hydrolysis of the corresponding compounds wherein X and/or Z is a cyano group, for example by subjecting the cyano compounds to the action of 95% sulphuric acid at 0° C.

The N-acyl compounds referred to above can be obtained by treating the appropriately substituted 2-aminothiophene with an acylating agent such as an acid anhydride or acid chloride, for example acetic anhydride or acetyl chloride when the N-acetyl derivatives are obtained, or with a mixture of formic acid and acetic anhydride when the N-formyl derivative is obtained. The appropriately substituted 2-aminothiophene used as starting materials to prepare the compounds of the present invention are themselves known compounds and are obtained by the conventional methods for the production of thiophene derivatives.

As specific examples of the compounds of the invention there may be mentioned 2-amino-3-(methylsulphonyl- or phenyl-sulphonyl)-5-nitrothiophene, 2-amino-5-nitrothiophene-3-carboxylic acid and its esters thereof with methanol, ethanol, n-butanol, n-propanol, β-ethoxyethanol and β-methoxyethanol, 2-amino-3-cyano-4-methyl-5-carbonamidothiophene and 2-amino-3-cyano-4-methyl-5-carbonamidothiophene and 2-amino-3-carbethoxy-4-(nitrophenyl)-5-nitrothiophene.

A preferred class of the compounds of the invention are the compounds of the formula:

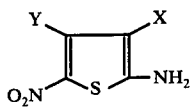

wherein X and Y have the meanings stated, and preferably Y is hydrogen or lower alkyl and X is lower alkoxy carbonyl.

The compounds of the invention are valuable as diazo components in the production of azo dyestuffs, particularly of disperse azo dyestuffs, or as biocides for the control of microorganisms such as bacteria, slimes and moulds. For this latter purpose the compounds are preferably used in the form of aqueous dispersions which optionally contain organic liquids and/or dispersing agents.

The invention is illustrated but not limited by the following Examples in which the parts and percentages are by weight.

EXAMPLE 1

213 Parts of 2-acetylamino-3-ethoxycarbonylthiophene are dissolved in 2000 parts of sulphuric acid at 0° − 10° C, and a mixture of 67 parts of nitric acid (sp.gr. 1.50) and 200 parts of sulphuric acid is slowly added, the temperature being maintained between 0° and 5° C by external cooling. The mixture is then poured into ice and water and the precipitated 2-acetylamino-3-ethoxycarbonyl-5-nitrothiophene (m.p.t. 144° C) is filtered off. The solid is stirred for 24 hours in a mixture of 200 parts of ethanol and 90 parts of sulphuric acid at 80° C, the solution is cooled and the precipitated 2-amino-3-ethoxycarbonyl-5-nitrothiophene filtered off, washed with ethanol and then with water and dried. The product melts at 240° to 242° C.

The 2-acetylamino-3-ethoxycarbonylthiophene was itself obtained by heating 2-amino-3-ethoxycarbonylthiophene with acetic anhydride.

In place of the 2-acetylamino-3-ethoxycarbonylthiophene used in the above Example there is used an equivalent amount of 2-formylamino-3-ethoxycarbonylthiophene (which was obtained by treating 2-amino-3-ethoxycarbonylthiophene with a mixture of formic acid and acetic anhydride) when 2-amino-3-ethoxycarbonyl-5-nitrothiophene is also obtained.

2-Amino-3-methoxycarbonyl-5-nitrothiophene (m.p.t. 227° C), 2-amino-3-ethoxycarbonyl-4-methyl-5-nitrothiophene (m.p.t. 204° C) and 2-amino-3-isobutoxycarbonyl-5-nitrothiophene (m.p.t. 138° C) are prepared in similar manner by the nitration of 2-acetylamino-3-methoxycarbonylthiophene, 2-acetylamino-3-ethoxycarbonyl-4-methylthiophene and 2-acetylamino-3-isobutoxycarbonylthiophene respectively.

EXAMPLE 2

A mixture of 1.5 parts of nitric acid (sq. gr. 1.50), 2 parts of acetic acid and 2 parts of acetic anhydride is added over 30 minutes to a suspension of 5 parts of 2-formylamino-3-cyanothiophene (obtained by treating 2-amino-3-cyanoethiophene with a mixture of formic acid and acetic anhydride) in 20 parts of acetic acid, the temperature of the mixture being maintained between 35° and 40° C. The mixture is poured into ice and water; sodium acetate added to remove mineral acidity, and the mixture stirred until no acetic anhydride remains. The resulting 2-formylamino-3-cyano-5-nitrothiophene (m.pt 216° − 218° C) is deacylated by heating in an 8% solution of sulphuric acid in ethanol at 80° C.

EXAMPLE 3

In place of the 2-acetylamino-3-ethoxycarbonylthiophene used in Example 1 there is used an equivalent amount of 2-formyl-aminothiophene-3-carboxylic acid whereby there is obtained 2-amino-5-nitrothiophene-3-carboxylic acid of m.pt above 310° C.

EXAMPLE 4

28.9 Parts of 2-acetylamino-3-ethoxycarbonyl-4-phenylthiophene are gradually added to a mixture of 130 parts of sulphuric acid and 13.5 parts of nitric acid (sp. gr. 1.50) at −5° C. The mixture is stirred for 1 hour at −5° to 0° C, and is then poured into 1700 parts of ice and water. The precipitated solid is filtered off and is heated for 1 hour in a 8% solution of sulphuric acid in ethanol at 80° C. The solution is cooled, and the solid filtered off, washed and dried. The solid consists of a mixture of 2-amino-3-ethoxycarbonyl-4-(o-nitrophenyl)-5-nitrothiophene and 2-amino-3-ethoxycarbonyl-4-(p-nitrophenyl)-5-nitrothiophene.

When the nitration is carried out in acetic anhydride as medium instead of sulphuric acid, the resulting product is 2-amino-3-ethoxycarbonyl-4-phenyl-5-nitrothiophene.

EXAMPLE 5

10 Parts of 2-acetylamino-3-ethoxycarbonyl-5-nitrothiophene (obtained as described in Example (1) is dissolved in 50 parts of β-methoxyethanol containing 1 part of tetra-n-butyltitanate and the mixture heated for 10 hours at the boil. The mixture is cooled, 50 parts of water added and the precipitated 2-acetylamino-3-(β-methoxyethoxycarbonyl)-5-nitrothiophene (m.pt 112° − 113° C) is filtered off and dried. Hydrolysis of this compound in a hot 4.5% solution of sulphuric acid in ethanol gives 2-amino-3-(β-methoxyethoxycarbonyl)-5-nitrothiophene.

EXAMPLE 6

A mixture of 10 parts of 2-amino-3-ethoxycarbonyl-5-nitrothiophene, 100 parts of n-butanol and 1 part of tetra-n-butyltitanate is stirred for 18 hours at the boil. The mixture is cooled and the precipitated 2-amino-3-n-butyloxycarbonyl-5-nitrothiophene (m.p. 136° − 139° C) is filtered off, washed with methanol and dried. The corresponding n-heptyl ester, prepared in similar manner from n-heptanol, melted at 86° – 89° C.

EXAMPLE 7

A mixture of 18.7 parts of acetoacetanilide, 90 parts of ethanol, 3.2 parts of sulphur, 13.5 parts of ethylcyanoacetate and 7 parts of diethylamine is stirred for 6 hours at the boil. The mixture is cooled and the precipitated 2-amino-3-carboethoxy-4-methyl-5-N-phenylcarbamoyl-thiophene (m.pt 174° – 176° C) is filtered off, washed with ethanol and dried.

EXAMPLE 8

In place of the 2-acetylamino-3-ethoxycarbonylthiophene used in Example 1 there is used an equivalent amount of 2-formylamino-3-carbonamidothiophene and the nitration is carried out at −10° to −5° C, 2-amino-3-carbonamido-5-nitrothiophene (m.p 266° – 268° C) is obtained.

EXAMPLE 9

A mixture of 21.6 parts of 2-formylamino-5-nitrothiophene-3-carboxylic acid, 11.9 parts of thionyl chloride and 500 parts of toluene is stirred at the boil for 2 hours. The mixture is filtered, the filtrate cooled to 5° C and 14.6 parts of diethylamine added. The mixture is stirred for 1 hour, and the precipitated 2-formylamino-3-N:N-diethylcarbonamido-5-nitrothiophene filtered off. This on treatment in a hot 5% solution of sulphuric acid in ethanol gave 2-amino-3-N:N-diethylcarbonamido-5-nitrothiophene.

EXAMPLE 10

A mixture of 22.7 parts of 2-acetylamino-3-ethoxycarbonyl-4-methylthiophene, 261 parts of N-methylformanilide and 28.4 parts of phosphoryl chloride is stirred for 90 minutes at 90° – 95° C. 300 Parts of a 4N aqueous solution of sodium acetate are added and the mixture stirred for 10 minutes at 90° C. The oily solid is separated from the liquid and crystallised from ethanol to give 2-acetylamino-3-ethoxycarbonyl-4-methyl-5-formylthiophene (m.pt 174° – 176° C).

A mixture of 12.7 parts of this thiophene compound, 6.95 parts of hydroxylamine hydrochloride, 10.1 parts of sodium bicarbonate, 300 parts of ethanol and 50 parts of water is stirred for 90 minutes at the boil, filtered, the filtrate cooled, and the oxime (m.pt 214° C) which separated out isolated. A mixture of 8.5 parts of the oxime and 30 parts of acetic anhydride is stirred at the boil for 30 minutes, then added to 200 parts of water and the 2-acetylamino-3-ethoxycarbonyl-4-methyl-5-cyanoethiophene isolated. Subsequent hydrolysis in aqueous alkaline medium gave 2-amino-3-ethoxycarbonyl-4-methyl-5-cyanoethiophene.

EXAMPLE 11

In place of the 2-acetylamino-3-ethoxycarbonyl-4-phenylthiophene used in Example 4 there is used an equivalent amount of 2-acetylamino-3-phenylsulphonylthiophene (which was obtained by condensing phenylsulphonylacetonitrile with 2:5-dihydroxy-1:4-dithiane in ethanol containing piperidine and subsequently acetylating) whereby 2-amino-3-phenylsulphonyl-5-nitrothiophene (m.pt 155° – 157° C) is obtained.

EXAMPLE 12

A solution of 1 part of 2-amino-3-ethoxycarbonyl-4-methyl-5-cyanothiophene in 10 parts of sulphuric acid is maintained for 24 hours at 0° C. The solution is poured into water, and the precipitated 2-amino-3-ethoxycarbonyl-4-methyl-5-carbonamido thiophene filtered off and dried.

We claim:

1. A compound of the formula:-

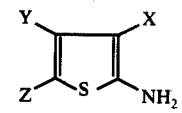

wherein X is selected from the group consisting of lower alkyl sulphonyl, phenylsulphonyl, cyano, carboxylic acid, lower alkoxycarbonyl, lower alkoxy lower alkoxycarbonyl and carbonamido of the formula

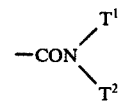

wherein $T^1$ is selected from hydrogen, lower alkyl and phenyl, and $T^2$ is selected from hydrogen and lower alkyl;

Y is selected from hydrogen, lower alkyl, phenyl and nitrophenyl;

and Z is selected from the group consisting of nitro, cyano and carbonamido of the formula

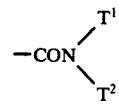

wherein $T^1$ is selected from hydrogen, lower alkyl and phenyl, and $T^2$ from hydrogen and lower alkyl.

2. A compound as claimed in claim 1 wherein X is selected from the group consisting of cyano, carboxylic acid, lower alkoxycarbonyl, lower alkoxy lower alkoxycarbonyl and carbonamido of the formula

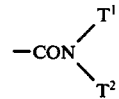

wherein $T^1$ is selected from hydrogen, lower alkyl and phenyl, and $T^2$ is selected from hydrogen and lower alkyl.

3. A compound of the formula

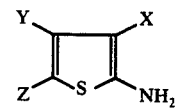

wherein X is selected from the group consisting of lower alkoxy carbonyl and lower alkoxy lower alkoxycarbonyl;

Y is selected from the group consisting of hydrogen, lower alkyl, phenyl and nitrophenyl; and Z is selected from the group consisting of nitro, cyano and carbonamido of the formula

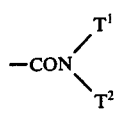

wherein T¹ is selected from hydrogen, lower alkyl and phenyl, and T² is selected from the group consisting of hydrogen and lower alkyl.

4. A compound of the formula

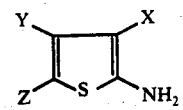

wherein
X is selected from the group consisting of lower alkoxycarbonyl and lower alkoxy lower alkoxy carbonyl;
Y is selected from the group consisting of hydrogen, lower alkyl, phenyl and nitrophenyl; and
Z is nitro.
5. A compound as claimed in claim 4 wherein X is lower alkoxycarbonyl, Y is hydrogen and Z is nitro.
6. A compound as claimed in claim 4 wherein X is lower alkoxycarbonyl, Y is lower alkyl and Z is nitro.

* * * * *